(12) United States Patent
Tan et al.

(10) Patent No.: US 8,802,070 B2
(45) Date of Patent: Aug. 12, 2014

(54) COMPOSITIONS CONTAINING A PHOSPHOLIPID, A NONIONIC SURFACTANT, AND AN ANIONIC SILICONE FOR LIFTING COLOR AND/OR IMPARTING SHINE ONTO KERATINOUS SUBSTRATES

(75) Inventors: Siliu Tan, Westfield, NJ (US); Nghi Van Nguyen, Edison, NJ (US); Sawa Hashimoto, Garwood, NJ (US)

(73) Assignee: L'Oreal, Paris (FR)

( * ) Notice: Subject to any disclaimer, the term of this patent is extended or adjusted under 35 U.S.C. 154(b) by 55 days.

(21) Appl. No.: 13/167,954

(22) Filed: Jun. 24, 2011

(65) Prior Publication Data

US 2012/0325253 A1    Dec. 27, 2012

(51) Int. Cl.
*A61Q 5/10*    (2006.01)

(52) U.S. Cl.
USPC ...................... 424/70.6; 424/70.31

(58) Field of Classification Search
None
See application file for complete search history.

(56) References Cited

U.S. PATENT DOCUMENTS

| | | | |
|---|---|---|---|
| 4,157,388 A | 6/1979 | Christiansen | |
| 4,702,906 A | 10/1987 | Jacquet et al. | |
| 4,719,282 A | 1/1988 | Nadolsky et al. | |
| 4,823,985 A | 4/1989 | Grollier et al. | |
| 5,070,171 A | 12/1991 | O'Lenick, Jr. | |
| 5,093,452 A | 3/1992 | O'Lenick, Jr. | |
| 5,149,765 A | 9/1992 | O'Lenick, Jr. | |
| 5,248,783 A | 9/1993 | O'Lenick | |
| 5,739,371 A | 4/1998 | O'Lenick, Jr. | |
| 6,616,706 B1 | 9/2003 | Kahre et al. | |
| 7,449,029 B2 | 11/2008 | Nguyen et al. | |
| 7,608,569 B2 | 10/2009 | Nguyen et al. | |
| 7,727,288 B2 | 6/2010 | Nguyen et al. | |
| 2006/0286055 A1 | 12/2006 | Cannell et al. | |
| 2006/0286056 A1 | 12/2006 | Cannell et al. | |
| 2006/0286057 A1 | 12/2006 | Cannell et al. | |
| 2006/0292100 A1 | 12/2006 | Nguyen et al. | |
| 2007/0110691 A1 | 5/2007 | Nguyen et al. | |
| 2008/0085253 A1 | 4/2008 | Nguyen et al. | |
| 2008/0085254 A1 | 4/2008 | Nguyen et al. | |
| 2008/0085255 A1 | 4/2008 | Nguyen et al. | |
| 2008/0085258 A1 | 4/2008 | Nguyen et al. | |
| 2008/0095725 A1 | 4/2008 | Nguyen et al. | |
| 2008/0095726 A1 | 4/2008 | Nguyen et al. | |
| 2008/0095727 A1 | 4/2008 | Nguyen et al. | |
| 2008/0095728 A1 | 4/2008 | Nguyen et al. | |
| 2008/0095729 A1 | 4/2008 | Nguyen et al. | |
| 2008/0096781 A1 | 4/2008 | Nguyen et al. | |
| 2008/0096782 A1 | 4/2008 | Nguyen et al. | |
| 2008/0097070 A1 | 4/2008 | Nguyen et al. | |
| 2008/0233072 A1 * | 9/2008 | Bureiko et al. | 424/70.122 |
| 2009/0053161 A1 | 2/2009 | Nguyen et al. | |
| 2010/0154140 A1 | 6/2010 | Simonet et al. | |

FOREIGN PATENT DOCUMENTS

| | | |
|---|---|---|
| EP | 80976 | 11/1982 |
| EP | 122324 | 11/1983 |
| FR | 2586913 | 9/1985 |
| GB | 1073947 | 9/1964 |

OTHER PUBLICATIONS

U.S. Appl. No. 13/167,779, filed Jun. 24, 2011, Sawa Hashimoto.
U.S. Appl. No. 13/167,781, filed Jun. 24, 2011, Sawa Hashimoto.
U.S. Appl. No. 13/167,788, filed Jun. 24, 2011, Sawa Hashimoto.
U.S. Appl. No. 13/167,791, filed Jun. 24, 2011, Sawa Hashimoto.
U.S. Appl. No. 13/167,796, filed Jun. 24, 2011, Sawa Hashimoto.
U.S. Appl. No. 13/167,803, filed Jun. 24, 2011, Sawa Hashimoto.
U.S. Appl. No. 13/276,479, filed Oct. 19, 2011, Sawa Hashimoto.
U.S. Appl. No. 13/167,811, filed Jun. 24, 2011, Sawa Hashimoto.
U.S. Appl. No. 13/276,491, filed Oct. 19, 2011, Sawa Hashimoto.
U.S. Appl. No. 13/167,825, filed Jun. 24, 2011, Sawa Hashimoto.
U.S. Appl. No. 13/167,837, filed Jun. 24, 2011, Sawa Hashimoto.
U.S. Appl. No. 13/167,847, filed Jun. 24, 2011, Sawa Hashimoto.
U.S. Appl. No. 13/276,499, filed Oct. 19, 2011, Sawa Hashimoto.
U.S. Appl. No. 13/167,877, filed Jun. 24, 2011, Sawa Hashimoto.
U.S. Appl. No. 13/167,882, filed Jun. 24, 2011, Sawa Hashimoto.
U.S. Appl. No. 13/167,893, filed Jun. 24, 2011, Sawa Hashimoto.
U.S. Appl. No. 13/167,897, filed Jun. 24, 2011, Siliu Tan.
U.S. Appl. No. 13/167,903, filed Jun. 24, 2011, Siliu Tan.
U.S. Appl. No. 13/167,921, filed Jun. 24, 2011, Siliu Tan.
U.S. Appl. No. 13/167,938, filed Jun. 24, 2011, Siliu Tan.
U.S. Appl. No. 13/167,948, filed Jun. 24, 2011, Siliu Tan.
U.S. Appl. No. 13/167,954, filed Jun. 24, 2011, Siliu Tan.
U.S. Appl. No. 13/167,966, filed Jun. 24, 2011, Siliu Tan.
U.S. Appl. No. 13/167,972, filed Jun. 24, 2011, Siliu Tan.
U.S. Appl. No. 13/167,988, filed Jun. 24, 2011, Siliu Tan.
U.S. Appl. No. 13/168,000, filed Jun. 24, 2011, Siliu Tan.
U.S. Appl. No. 13/168,019, filed Jun. 24, 2011, Siliu Tan.
McCutcheon's "Detergent and Emulsifiers", North American Edition (1986), Published by Allured Publishing Corporation.
McCutcheon's "Functional Materials", North American Edition (1992).
Walter Noll "Chemistry and Technology of Silicones" (1968), Academic Press.
Todd Byers "Volatile Silicone Fluids for Cosmetics", Cosmetics and Toiletries, vol. 91, Jan. 1976, pp. 29-32.

* cited by examiner

*Primary Examiner* — Jyothsna Venkat

(74) *Attorney, Agent, or Firm* — L'Oreal USA

(57) ABSTRACT

The present invention is drawn to a composition and method for lifting color and/or imparting shine onto keratinous substrates, the composition containing: (a) at least one phospholipid; (b) at least one nonionic surfactant; (c) at least one anionic silicone; and (d) at least one oxidizing agent. The compositions of the present invention may optionally contain at least one thickening agent, at least one alkaline agent, at least one fatty substance other than a fatty acid, and at least one salt.

18 Claims, No Drawings

COMPOSITIONS CONTAINING A PHOSPHOLIPID, A NONIONIC SURFACTANT, AND AN ANIONIC SILICONE FOR LIFTING COLOR AND/OR IMPARTING SHINE ONTO KERATINOUS SUBSTRATES

FIELD OF THE INVENTION

The present invention relates to novel compositions for lightening the color of hair and for imparting shine based on a combination of at least one phospholipid, at least one nonionic surfactant, at least one anionic silicone, and at least one oxidizing agent.

BACKGROUND OF THE INVENTION

It is known that consumers desire to use cosmetic and personal care compositions that enhance the appearance of keratinous substrates such as hair and skin by changing the color of the hair or skin and/or by imparting various properties to hair or skin such as shine and conditioning. The process of changing the color of hair can involve either depositing an artificial color onto the hair which provides a different shade or color to the hair or lifting the color of the hair, such as for example, from a dark brown shade to a medium brown or a light brown shade.

The process of lifting the color of keratinous substrates such as hair, also known as lightening, generally requires the use of compositions that comprise at least one oxidizing agent. The role of this oxidizing agent is to break down the melanin of hair, which, depending on the nature of the oxidizing agent present, results in a more or less pronounced lightening of the color of hair fibers. In certain instances, hair lightening compositions may possess an alkalinity such that these compositions may have a pH value of above 7 and may require the presence of an alkaline agent.

In order to improve the performance of compositions for lifting color, the use of new and additional ingredients and novel combinations of ingredients are continuously sought; however, the choice of ingredients could pose difficulties insofar as they must improve the lifting capability of the composition without being detrimental to other properties of the composition such as its application, rheology or viscosity properties and/or resulting into more disadvantages such as increased damage or a less healthy look to the hair. It is therefore, important to provide the consumer with a hair lightening or lifting composition and method that can lift the color of the hair in an efficient manner, not only to the degree of lift desired, but also with the added benefit of obtaining better lift compared to current products and methods without resulting in more damage to the hair. At the same time, it is also desirable that such a composition and method can provide other advantageous properties to the hair such as shine, conditioning, and a healthy appearance to the hair. Furthermore, it is preferable to formulate such compositions that are less costly to manufacture by requiring less ingredients and/or lower levels of ingredients.

Thus, the objective of the present invention is to obtain novel compositions for lifting or lightening the color of the hair. Another objective of the invention is to obtain compositions that impart desirable shine to the hair and other advantages to the hair such as conditioning, a healthy appearance and less damage to the hair. Finally, it is an objective of the present invention to provide a composition that effectively lifts color with lowered cost of production.

BRIEF SUMMARY OF THE INVENTION

In order to achieve these and other advantages, the present invention is drawn to a ready-to-use aqueous composition for lifting color and/or imparting shine onto keratinous substrates containing, in a cosmetically acceptable medium,
a) at least one phospholipid;
b) at least one nonionic surfactant;
c) at least one anionic silicone;
e) optionally, at least one thickening agent;
f) optionally, at least one alkaline agent;
g) optionally, at least one fatty substance other than a fatty acid; and
h) optionally, at least one salt.

The present invention is also drawn to methods of lifting color and/or imparting shine onto keratinous substrates, comprising applying onto the keratinous substrates the above-disclosed ready-to-use aqueous composition.

Furthermore, the present invention is drawn to a kit for lifting color and/or imparting shine onto keratinous substrates.

DETAILED DESCRIPTION OF THE INVENTION

Other than in the operating examples, or where otherwise indicated, all numbers expressing quantities of ingredients and/or reaction conditions are to be understood as being modified in all instances by the term "about" which encompasses±10%.

"At least one" as used herein means one or more and thus includes individual components as well as mixtures/combinations.

"Keratinous substrate" may be chosen from, for example, hair, skin, eyelashes, eyebrows, lips and nails.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Polymers," as defined herein, include homopolymers and copolymers formed from at least two different types of monomers.

The term "substantially free of ammonia" as defined herein means that the composition of the present invention is either completely free of ammonia (including ammonium ions) or contains no appreciable amount of ammonia (including ammonium ions), for example, no more than 1% by weight, or no more than 0.5% by weight, or no more than 0.3% by weight, or no more than 0.1% by weight, based on the weight of the composition.

It has been surprisingly and unexpectedly discovered that the above-disclosed compositions and method lifted or lightened the color of hair effectively and/or imparted desirable shine to the hair.

Phospholipid

The phospholipids of the present invention are chosen from organic phospholipids. Particularly preferred organic phospholipids for use in the present invention include lecithins. Lecithins are mixtures of phospholipids, i.e., of diglycerides of fatty acids linked to an ester of phosphoric acid. Preferably, lecithins are diglycerides of stearic, palmitic, and oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids.

The lecithin used in the present invention may be present in the form of a liquid, powder, or granules. Lecithins useful in the invention include, but are not limited to, soy lecithin and hydroxylated lecithin. For example, ALCOLEC S is a fluid soy lecithin, ALCOLEC F 100 is a powder soy lecithin, and ALCOLEC Z3 is a hydroxylated lecithin, all of which are available from the American Lecithin Company.

Other than lecithins, additional examples of phospholipids which may be useful in the present invention include, but are not limited to, multifunctional biomimetic phospholipids. For example, the following multifunctional biomimetic phospholipids manufactured by Uniqema Industries may be useful: cocamidopropyl PG-dimonium chloride phosphate (PHOSPHOLIPID PTC), sodium coco PG-dimonium chloride phosphate (PHOSPHOLIPID CDM), stearamidopropyl PG-dimonium chloride phosphate (PHOSPHOLIPID SV), sodium borageamidopropyl PG-dimonium chloride phosphate (PHOSPHOLIPID GLA), linoleamidopropyl PG-dimonium chloride phosphate (PHOSPHOLIPID EFA) and those biomimetic phospholipids belonging to the Arlasilk® Phospholipid series. A particularly preferred multifunctional biomimetic phospholipid for use in the present invention is linoleamidopropyl PG-dimonium chloride phosphate.

In the present invention, the at least one phospholipid is preferably used in an amount of from about 0.01% to about 20% by weight, preferably about 0.5% to about 10% by weight, and more preferably from about 1% to about 5% by weight, based on the total weight of the composition.

Nonionic Surfactants

In general, nonionic surfactants having a Hydrophilic-Lipophilic Balance (HLB) of from 8 to 20, are contemplated for use by the present invention. Nonlimiting examples of non-ionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

Preferred nonionic surfactants are those formed from a fatty alcohol, a fatty acid, or a glyceride with a $C_4$ to $C_{36}$ carbon chain, preferably a $C_{12}$ to $C_{18}$ carbon chain, more preferably a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 8. Preferably the nonionic surfactants contain ethoxylate in a molar content of from 10-25, more preferably from 10-20 moles.

The nonionic surfactant will typically be present in the composition in an amount of from about 0.1% to about 70% by weight, preferably from about 0.5% to 50% by weight, and more preferably from about 0.5% to about 30% by weight, and even more preferably from about 1% to about 20% by weight, based on the total weight of the composition.

Anionic Silicone

In general, non-limiting examples of anionic silicones which may be used in the present invention include silicone carboxylates, silicone phosphates, silicone sulfates, silicone sulfosuccinates, and silicone sulfonates.

Suitable silicone carboxylates may be chosen from water soluble silicone compounds comprising at least one carboxylic acid group, oil soluble silicone compounds comprising at least one carboxylic acid group, water-dispersible silicone compounds comprising at least one carboxylic acid group, and silicone compounds comprising at least one carboxylic acid group which are soluble in organic solvents. In one embodiment, the at least one silicone compound comprising at least one carboxylic acid group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The at least one carboxylic acid group may be chosen from terminal carboxylic acid groups and pendant carboxylic acid groups. Further, the at least one carboxylic acid may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In one embodiment, the at least one silicone compound comprising at least one carboxylic acid group is chosen from silicone compounds of formula (I) and salts thereof:

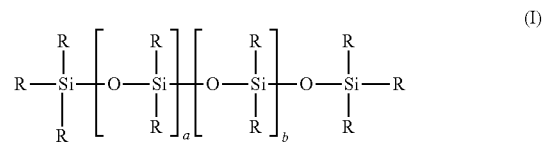

wherein: a is an integer ranging from 1 to 100; b is an integer ranging from 0 to 500; R, which may be identical or different, are each chosen from optionally substituted hydrocarbon groups comprising from 1 to 9 carbon atoms, optionally substituted phenyl groups, and groups of formula (II):

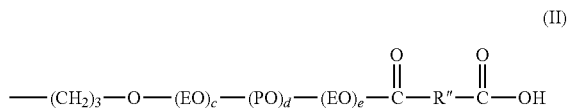

wherein: c, d, and e, which may be identical or different, are each integers ranging from 0 to 20; EO is an ethylene oxide group; PO is a propylene oxide group; and R" is chosen from optionally substituted divalent hydrocarbons, such as alkylene groups and alkenylene groups comprising from 2 to 22 carbon atoms, and optionally substituted divalent aromatic groups, such as groups of formula (III):

and groups of formula (IV):

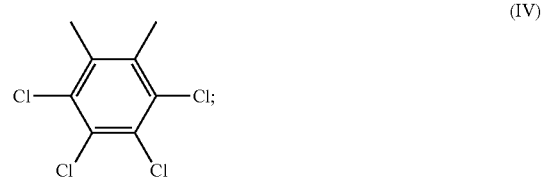

with the proviso that at least one of the R groups is chosen from groups of formula (II) and with the further proviso that when only one of the R groups is chosen from groups of formula (II), the other R groups are not all methyl groups.

Non-limiting examples of the at least one silicone compound include those commercially available from Noveon under the name Ultrasil® CA-1 Silicone and Ultrasil CA-2 Silicone, both of which correspond to formula (V) below. This silicone carboxylate is sold in the free acid form as an emulsifier and dispersing aid for complexing fatty cationic amines and quaternary amines. Thus, in one embodiment, the at least one silicone compound is chosen from silicone compounds of formula (V) and salts thereof:

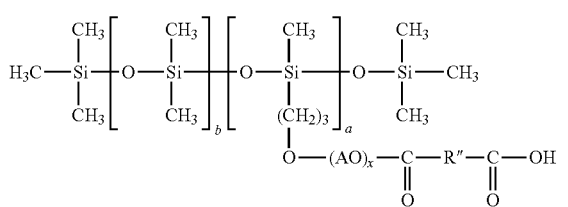

(V)

wherein: a is an integer ranging from 1 to 100; b is an integer ranging from 0 to 500; AO is chosen from groups of formula (VI):

(VI)

wherein: c, d, and e, which may be identical or different, are each integers ranging from 0 to 20; EO is an ethylene oxide group; and PO is a propylene oxide group; is an integer ranging from 0 to 60; R" is chosen from optionally substituted divalent hydrocarbons, such as alkylene groups and alkenylene groups comprising from 2 to 22 carbon atoms, and optionally substituted divalent aromatic groups, such as groups of formula (III):

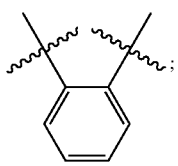

(III)

and groups of formula (IV):

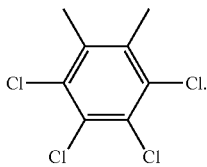

(IV)

Non-limiting examples of the at least one silicone compound include those described in U.S. Pat. Nos. 5,248,783 and 5,739,371, the disclosures of which are incorporated herein by reference, and which are silicone compounds of formula (I).

Suitable silicone phosphates may be chosen from water-soluble silicone compounds comprising at least one phosphate group, oil soluble silicone compounds comprising at least one phosphate group, water-dispersible silicone compounds comprising at least one phosphate group, and silicone compounds comprising at least one phosphate group which are soluble in organic solvents.

In one embodiment, the at least one silicone compound comprising at least one phosphate group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups ("EO"=—$CH_2$—$CH_2$—O—) and propylene oxide groups ("PO"=$C_3H_6O$).

The at least one phosphate group may be chosen from terminal phosphate groups and pendant phosphate groups. Further, the at least one phosphate group may be chosen from groups of formula —O—P(O)(OH)$_2$, groups of formula —O—P(O)(OH)(OR), and groups of formula —O—P(O)(OR)$_2$, wherein R may be chosen from H, inorganic cations, and organic cations. Non-limiting examples of inorganic cations include alkali metals, such as, for example, potassium lithium, and sodium. A non-limiting example of organic cations is at least one additional silicone compound which may be identical to or different from the at least one silicone compound bonded to the other oxygen of the phosphate group.

In one embodiment, the at least one silicone compound comprising at least one phosphate group is chosen from silicone compounds of formula (VII):

(VII)

wherein $R^1$, which may be identical or different, are each chosen from H, organic cations, inorganic cations, optionally substituted hydrocarbons (such as alkyl groups and alkenyl groups comprising from 1 to 22 carbon atoms), optionally substituted aromatic groups; groups of formula (VIII) and salts thereof:

(VIII)

wherein: c, and d, which may be identical or different, are each integers ranging from 0 to 20; e is an integer ranging from 0 to 19; and x is an integer ranging from 0 to 21; groups of formula (IX) and salts thereof:

(IX)

wherein: c, d, and e, which may be identical or different, are each integers ranging from 0 to 20; and x is an integer ranging from 0 to 21; and groups of formula (X) and salts thereof:

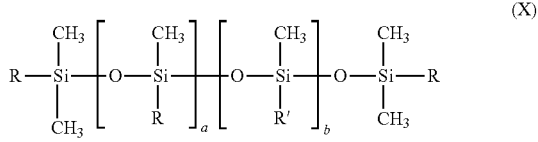

(X)

wherein: a is an integer ranging from 0 to 200; b is an integer ranging from 0 to 200; R', which may be identical or different, are each chosen from optionally substituted hydrocarbons, such as alkyl groups and alkenyl groups comprising from 1 to 22 carbon atoms, optionally substituted aromatic groups, groups of formula (IX) as defined above and salts thereof; and R, which may be identical or different, are each chosen from optionally substituted hydrocarbons, such as alkyl groups and alkenyl groups comprising from 1 to 22 carbon atoms, optionally substituted aromatic groups, optionally substituted divalent hydrocarbons, such as alkylene groups and alkenylene groups comprising from 1 to 22 carbon atoms, optionally substituted divalent aromatic groups, groups of formula (IX) as defined above and salts thereof, and groups of formula (XI):

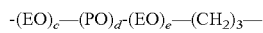  (XI)

wherein:

the $(CH_2)_3$ end is bonded to the silicon of the compound of formula (X) and the (EO) or (PO) end, if present, is bonded to the oxygen of the compound of formula (VII); c, d, and e, which may be identical or different, are each integers ranging from 0 to 20; EO is an ethylene oxide group; and PO is a propylene oxide group; and with the proviso that at least one R is chosen from groups of formula (XI) and salts thereof; and with the further proviso that at least one $R^1$ is chosen from groups of formula (X) and salts thereof and at least one other $R^1$ is chosen from H, organic cations, and inorganic cations.

Non-limiting examples of the inorganic cations include alkali metals, such as potassium, lithium, and sodium. Non-limiting examples of the at least one silicone compound include those commercially available from Phoenix Chemical, Inc. of New Jersey under the name of Pecosil®, such as Pecosil® PS-100, Pecosil® PS-112, Pecosil® PS-150, Pecosil® PS-200, Pecosil®, WDS-100, Pecosil® WDS-200, Pecosil® PS-100 B, and Pecosil® PS-100 K and those commercially available from Siltech under the name Silphos A-100 and Silphos A-150. Other non-limiting examples of the at least one silicone compound include those described in U.S. Pat. Nos. 5,070,171, 5,093,452, and 5,149,765 the disclosures of which are incorporated herein by reference.

Suitable silicone sulfates for use in the present invention include those represented by formula XII:

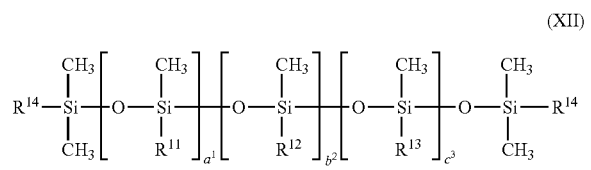  (XII)

wherein $R^{11}$ is selected from lower alkyl having one to eight carbon atoms or phenyl, $R^{12}$ is —$(CH_2)_3$—O-$(EO)_x$—$(PO)_y$-$(EO)_z$—$SO_3^{31}$-$M^+$ wherein M is a cation and is selected from Na, K, Li, or $NH_4$; x, y and z are integers independently ranging from 0 to 100; $R^{13}$ is —$(CH_2)_3$—O-$(EO)_x$—$(PO)_y$-$(EO)_z$—H; $R^{14}$ is methyl or hydroxyl; $a^1$ and $c^1$ are independently integers ranging from 0 to 50; $b^1$ is an integer ranging from 1 to 50. An example thereof is Ultrasil SA-1 silicone commercially available from Noveon.

Suitable silicone sulfosuccinates which may be employed include, but are not limited to, those corresponding to formula XIII:

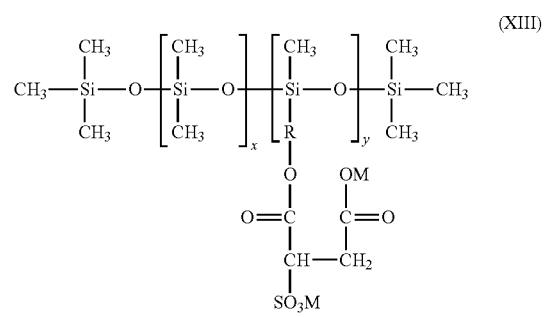  (XIII)

wherein R represents a divalent radical selected from

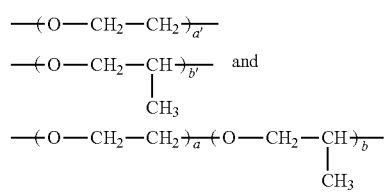

wherein a' and b' range from 0 to 30; x and y are such that the molecular weight ranges from 700 to 1600, and M is an alkali metal such as sodium or potassium, or an ammonium group.

A particularly preferred anionic silicone is Dimethicone PEG-7 phosphate, commercially available from Phoenix Chemical under the tradenames Pecosil® PS-100 and Pecosil® PS-112, and from Lubrizol Advanced Materials, Inc. under the tradename Silsense® PE-100L Silicone. Another particularly preferred anionic silicone is Dimethicone PEG-8 phosphate, commercially available from Lubrizol Advanced Materials, Inc. under the tradename Silsense® PE-100 Silicone.

The at least one anionic silicone is used in the present composition in an amount of from about 0.5% to about 40% by weight, preferably from about 1% to about 30% by weight, more preferably from about 2% to about 20% by weight, and even more preferably from about 3% to about 10% by weight, based on the total weight of the composition.

Oxidizing Agent

The compositions of the present invention require an oxidizing agent which may be chosen, for example, from a peroxide, a persulfate, a perborate, a percarbonate, alkali metal bromates, ferricyanides or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In one embodiment, the oxidizing agent is hydrogen peroxide present in an aqueous solution whose titre may range from 1 to 40 volumes, such as from 5 to 40 volumes or such as from 5 to 20 volumes.

In another embodiment, the oxidizing agent is a persulfate and/or a monopersulfate such as, for example, potassium persulfate, sodium persulfate, ammonium persulfate, as well as mixtures thereof. In one embodiment the oxidizing agents in the present disclosure are selected from hydrogen peroxide, potassium persulfate, sodium persulfate and mixtures thereof.

In general, the oxidizing agent will be present in an amount of from about 0.05 to about 40% by weight, such as from about 0.1% to about 30% by weight, or such as from about 0.1% to about 20% by weight, or such as from about 1% to about 10% by weight, based on the total weight of the composition.

Thickening Agent

Thickening agents of the present invention may be chosen from polymeric thickeners and non-polymeric thickeners as described in US2010154140A, herein incorporated by reference in its entirety.

Thickening agents of the present invention may be chosen from polymeric thickeners and non-polymeric thickeners. The at least one polymeric thickener can be chosen from ionic or non-ionic, associative or non-associative polymers. Exemplary polymeric thickeners include various native gums. Representative non-polymeric thickening agents include mineral salts such as sodium chloride; oxyethylenated molecules and especially ethoxylated alkyl or acyl derivatives of polyols. These polymers can be modified physically or chemically.

The at least one thickening agent of the present invention is preferably used in an amount of from greater than 0% to about 15% by weight, preferably from about 0.1% to about 10% by weight, and more preferably from about 1% to about 5% by weight, based on the total weight of the composition.

Alkaline Agents

The at least one alkaline agent of the present invention may be chosen from organic amines, organic amine salts, ammonium salts, and inorganic bases.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched $C_1$-$C_8$ alkyl groups bearing at least one hydroxyl radical.

Organic amines may also be chosen from alkanolamines such as mono-, di- or trialkanolamines, comprising one to three identical or different $C_1$-$C_4$ hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris(hydroxymethylamino)methane.

The organic amines correspond to the formula (XIV):

$$\begin{array}{c} Rx \\ \diagdown \\ \phantom{x}N-W-N \\ \diagup \phantom{xxxx} \diagdown \\ Ry \phantom{xxxxx} Rt \end{array} \phantom{xxx} Rz \phantom{x} (XIV)$$

wherein W is chosen from $C_1$-$C_6$ alkylene residues optionally substituted with a hydroxyl group or a $C_1$-$C_6$ alkyl radical; Rx, Ry, Rz and Rt, which may be identical or different, are chosen from a hydrogen atom, $C_1$-$C_6$ alkyl radicals, $C_1$-$C_6$ hydroxyalkyl radicals, and $C_1$-$C_6$ aminoalkyl radicals.

Examples of such amines that may be mentioned include but not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Further as non-limiting examples, the amino acids may be chosen from basic amino acids comprising an additional amine function optionally included in a ring or in a ureido function.

Such basic amino acids may be chosen from those corresponding to formula (A) below:

$$R-CH_2-CH\begin{array}{c} NH_2 \\ \diagup \\ \diagdown \\ CO_2H \end{array} \phantom{xx} (A)$$

wherein R is a group chosen from:

[imidazole ring structure with NH and N];

—$(CH_2)_3NH_2$;

—$(CH_2)_2NH_2$;

—$(CH_2)_2NHCONH_2$;

—$(CH_2)_2NH-\underset{\underset{NH}{\|}}{C}-NH_2$

The compounds corresponding to formula (A) may be chosen from histidine, lysine, arginine, ornithine, and citrulline.

Amino acids that may be used in the present disclosure include but not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

In some embodiments, the organic amines are chosen from basic amino acids. The amino acids may be chosen from, for instance, arginine, lysine and histidine, or mixtures thereof.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine; glycocyamine, metformin, agmatine, N-amidinoalanine, 3-guanidinopropionic acid, 4-guanidinobutyric acid, and 2-([amino(imino)methyl]amino)ethane-1-sulfonic acid.

As a non-limiting example, the organic amines are chosen from alkanolamines. For example, the organic amines are chosen from 2-amino-2-methyl-1-propanol and monoethanolamine, or mixtures thereof. Further as an example, the organic amine is monoethanolamine.

The alkaline agent may be an organic amine in salt form. The term "organic amine salt," as used herein, means organic or mineral salts of an organic amine as described above.

As a non-limiting example, the organic salts may be chosen from the salts of organic acids, such as citrates, lactates, glycolates, gluconates, acetates, propionates, fumarates, oxalates and tartrates.

Further as a non-limiting example, the mineral salts may be chosen from hydrohalides (for example hydrochlorides), carbonates, hydrogen carbonates, sulfates, hydrogen phosphates, and phosphates.

The ammonium salts that may be used in the composition according to the present disclosure may be chosen from the following acid salts: carbonate, bicarbonate. For instance, the salt is the carbonate, such as ammonium carbonate.

The inorganic bases that may be used in the composition according to the present disclosure may be chosen from alkali metal phosphates and carbonates such as, for example, sodium phosphate, potassium phosphate, sodium carbonate, sodium bicarbonate, potassium carbonate, potassium bicarbonate, and their derivatives.

The inorganic bases may also include alkali metals of carboxylates such as, for example, sodium acetate, potassium acetate, sodium citrate, and potassium citrate, and their derivatives.

According to at least one embodiment, the ready-to-use compositions of the present invention comprise an alkaline agent chosen from at least one organic amine such as at least one alkanolamine. In certain preferred embodiments, when the composition comprises more than one alkaline agent, including an alkanolamine and ammoniumhydroxides or salts thereof, the amount of organic amine(s) are, for example, higher than the amount of ammonia/ammonium hydroxide.

According to at least one embodiment, the ready-to-use compositions of the present invention contain a small amount of ammonia, or even no ammonia. According to this embodiment, the ready-to-use composition, for example, contains at least one alkanolamine such as monoethanolamine.

The at least one alkaline agent may be employed in the composition of the present invention in an amount ranging from about 0.01% to about 30% by weight, such as from about 0.1% to about 20% by weight, or such as from about 0.5% to about 15% by weight, or such as from about 1% to about 10% by weight, based on the total weight of the composition.

The pH of the ready-to-use composition according to the invention can range from about 2 to about 12, such as from about 7 to 12, or such as from about 7 to about 11 or such as from about 7.5 to about 10 or such as from about 2 to about 7 or such as from about 5 to about 7.

When the pH of the ready-to-use composition is at least 7, lift or lightening of the color of keratinous substrates and/or shine on keratinous substrates is achieved when the composition is applied onto the keratinous substrates. Conversely, when the pH of the ready-to-use composition is below 7, only shine on keratinous substrates may be achieved.

Fatty Substance

The composition of the present invention may further comprise at least one fatty substance other than a fatty acid.

"Fatty substance" means an organic compound insoluble in water at normal temperature (25° C.) and at atmospheric pressure (760 mmHg) (solubility below 5% and such as below 1% and further such as below 0.1%). Fatty substances have in their structure a chain of at least two siloxane groups or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

The composition of the present invention comprises at least 10% of fatty substances by weight relative to the total weight of the composition, these substances being other than fatty acid.

Fatty substances are, for example, chosen from lower alkanes, fatty alcohols, esters of fatty acid, esters of fatty alcohol, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

Non-limiting examples of non-silicone oils usable in the composition of the disclosure, include: hydrocarbon oils of animal origin, such as perhydrosqualene; hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam®. fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; non-afluoro-methoxybutane and nonafluoroethoxyisobutane; derivatives of perfluoromorpholine, such as 4-trifluoromethyl perfluoromorpholine sold under the name "PF 5052®" by the 3M Company.

The fatty alcohols usable as fatty substances in the composition of the disclosure include, but are not limited to, non-alkoxylated, saturated or unsaturated, linear or branched, and have from 6 to 30 carbon atoms and more particularly from 8 to 30 carbon atoms; For example, cetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol.

The exemplary non-silicone wax or waxes that can be used in the composition of the disclosure are chosen from carnauba wax, candelilla wax, and Alfa wax, paraffin wax, ozokerite, vegetable waxes such as olive wax, rice wax, hydrogenated jojoba wax or absolute waxes of flowers such as the essential wax of blackcurrant flower sold by the company BERTIN (France), animal waxes such as beeswaxes, or modified beeswaxes (cerabellina); other waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting mentions of esters can be made of the esters of $C_4$-$C_{22}$ di- or tricarboxylic acids and of $C_1$-$C_{22}$ alcohols and the esters of mono-, di- or tricarboxylic acids and of $C_2$-$C_{26}$ di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of $C_6$-$C_{30}$, such as $C_{12}$-$C_{22}$ fatty acids. "Sugar" as used in the disclosure means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids can, for example, be chosen from the esters or mixtures of esters of sugars described previously and of linear or branched, saturated or unsaturated $C_6$-$C_{30}$, such as $C_{12}$-$C_{22}$ fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof.

These esters can be for example oleate, laurate, palmitate, myristate, behenate, cocoate, stearate, linoleate, linolenate, caprate, arachidonates, or mixtures thereof such as the oleopalmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

Non-limiting mention can be made of the product sold under the name GLUCATE® DO by the company Amerchol, which is a dioleate of methylglucose.

Exemplary esters or of mixtures of esters of sugar of fatty acid include: the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the monolaurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Goldschmidt under the name TEGOSOFT® PSE.

The silicones usable in the composition of the present disclosure include but are not limited to volatile or non-volatile, cyclic, linear or branched silicones, modified or not with organic groups, having a viscosity from $5 \times 10^{-6}$ to 2.5 $m^2/s$ at 25° C., such as from $1 \times 10^{-5}$ to 1 $m^2/s$.

The silicones usable according to the disclosure can be in the form of oils, waxes, resins or gums.

In some embodiments, the silicone is chosen from the polydialkylsiloxanes, such as the polydimethylsiloxanes (PDMS), and the organo-modified polysiloxanes having at least one functional group selected from the poly(alkoxylated) groups, the amine groups and the alkoxy groups.

The organopolysiloxanes are defined in more detail in the work of Walter NOLL "Chemistry and Technology of Silicones" (1968), Academic Press. They can be volatile or non-volatile.

When they are volatile, the silicones are, for example, chosen from those with a boiling point between 60° C. and 260° C., and for further examples, chosen from:

the cyclic polydialkylsiloxanes having from 3 to 7, such as from 4 to 5 silicon atoms. It can be, for example, the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, and mixtures thereof.

Non-limiting mentions can also be made of the cyclocopolymers of the dimethylsiloxanes/methylalkylsiloxane type, such as SILICONE VOLATILE® FZ 3109 marketed by the company UNION CARBIDE, of the formula XV:

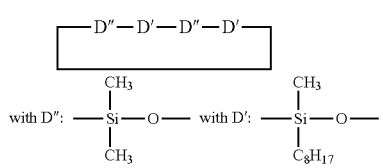
(XV)

with D'':  —Si(CH₃)(CH₃)—O—  with D':  —Si(CH₃)(C₈H₁₇)—O—

Non-limiting mentions can further be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy) bis-neopentane.

Other suitable volatile silicones include the linear volatile polydialkylsiloxanes having 2 to 9 silicon atoms and with a viscosity less than or equal to $5 \times 10^{-6}$ m$^2$/s at 25° C. An example is decamethyltetrasiloxane, marketed under the name "SH 200" by the company TORAY SILICONE. Silicones included in this class are also described in the article published in Cosmetics and Toiletries, Vol. 91, January 76, p. 27-32—TODD BYERS "Volatile Silicone fluids for cosmetics".

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones are, for example, chosen from the polydialkylsiloxanes, such as the polydimethylsiloxanes with trimethylsilyl end groups. The viscosity of the silicones is measured at 25° C. according to standard ASTM 445 Appendix C.

Among these polydialkylsiloxanes, mention can be made of, non-exhaustively, the following commercial products: the SILBIONE® oils of series 47 and 70 047 or the MIRASIL® oils marketed by RHODIA, for example the oil 70 047 V 500 000; the oils of the MIRASIL® series marketed by the company RHODIA; the oils of the 200 series from the company DOW CORNING such as DC200, with a viscosity of 60 000 mm$^2$/s; the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company GOLDSCHMIDT, which are polydialkyl ($C_1$-$C_{20}$) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane and mixtures thereof.

Products usable according to the disclosure are, for example, mixtures such as: mixtures formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING; mixtures of a polydimethylsiloxane gum and a cyclic silicone such as the product SF 1214 Silicone Fluid from the company GENERAL ELECTRIC, said product being a gum SF corresponding to a dimethicone, having a number-average molecular weight of 500,000, dissolved in the oil SF 1202 Silicone Fluid corresponding to decamethylcyclopentasiloxane; mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 m$^2$/s and an oil SF 96 with a viscosity of $5 \times 10^{-6}$ m$^2$/s. This product, for example, has 15% of gum SE 30 and 85% of oil SF 96.

The organopolysiloxane resins usable according to the disclosure include but are not limited to crosslinked siloxane systems containing the units: $R_2SiO_{2/2}$, $R_3SiO_{1/2}$, $RSiO_{3/2}$ and $SiO_{4/2}$ in which R represents an alkyl having 1 to 16 carbon atoms. For example, R denotes a $C_1$-$C_4$ lower alkyl group such as methyl.

Among these resins, non-limiting mention can be made of the product marketed under the name "DOW CORNING 593" or those marketed under the names "SILICONE FLUID SS 4230 and SS 4267" by the company GENERAL ELECTRIC, which are silicones of dimethyl/trimethyl siloxane structure.

Non-limiting mention can also be made of the resins of the trimethylsiloxysilicate type, such as those marketed under the names X22-4914, X21-5034 and X21-5037 by the company SHIN-ETSU.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkyl-arylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from $1 \times 10^{-5}$ to $5 \times 10^2$ m$^2$/s at 25° C.

Among these polyalkarylsiloxanes, non-limiting mentins can be made of the products marketed under the following names: the SILBIONE® oils of series 70 641 from RHODIA; the oils of the series RHODORSIL® 70 633 and 763 from RHODIA; the oil DOW CORNING 556 COSMETIC GRADE FLUID from DOW CORNING; the silicones of the PK series from BAYER such as the product PK20; the silicones of the series PN, PH from BAYER such as the products PN1000 and PH1000; certain oils of the SF series from GENERAL ELECTRIC such as SF 1023, SF 1154, SF 1250, SF 1265.

Among the organomodified silicones, non-limiting mention can be made of the polyorganosiloxanes having: polyoxyethylene and/or polyoxypropylene groups optionally with $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl ($C_{12}$)-methicone copolyol marketed by the company DOW CORNING under the name Q2 5200; substituted or'unsubstituted amine groups such as the products marketed under the name GP 4 Silicone Fluid and GP 7100 by the company GENESEE or the products marketed under the names Q2 8220 and DOW CORNING 929 or 939 by the company DOW CORNING. The substituted amine groups are, for example, $C_1$-$C_4$ aminoalkyl groups; alkoxylated groups, such as the product marketed under the name "SILICONE COPOLYMER F-755" by SWS SILICONES and ABIL WAX® 2428, 2434 and 2440 by the company GOLDSCHMIDT.

In some embodiments, the at least one fatty substance is neither alkoxylated, nor glycerolated.

For example, the at least one fatty substance is chosen from compounds that are liquid or pasty at room temperature and at atmospheric pressure.

For further example, the at least one fatty substance is a compound that is liquid at a temperature of 25° C. and at atmospheric pressure.

The at least one fatty substance is, for example, chosen from the lower alkanes, fatty alcohols, esters of fatty acid, esters of fatty alcohol, and oils such as non-silicone mineral, vegetable and synthetic oils, the silicones.

According to at least one embodiment, the at least one fatty substance is chosen from liquid paraffin, polydecenes, liquid esters of fatty acids and of fatty alcohols, and mixtures thereof, for example, the at least one fatty substance of the composition according to the disclosure can be non-silicone.

In some embodiments, the at least one fatty substance is chosen from alkanes, hydrocarbons and silicones.

The composition according to the disclosure comprises at least one fatty substance other than a fatty acid, which is present in the composition in an amount of at least 10% by weight relative to the total weight of the composition. For example, the concentration of fatty substances is from about 10 to about 80% by weight, such as from about 15 to about 65% by weight, further such as from about 20 to about 55% by weight, based on the total weight of the composition.

Salts

The at least one salt of the present invention may be chosen from alkali earth metal salts and metal salts.

Suitable alkali earth metal salts may be chosen from Lithium, Sodium, Potassium, Magnesium, Calcium, Barium salts.

Suitable metal salts may be chosen from Manganese, Iron, Copper, Silver, Zinc, Aluminum salts.

In some embodiments, the salt is a mono- or a divalent metal. In some embodiments, the metal salt is a salt of a transition metal. In other embodiments, the metal salt is not a salt of an alkali earth metal.

The at least one salt of the present invention may be also chosen from salt compounds having organic counterions and salt compounds having polyatomic counterions such as an ammonium ion or such as a substituted ammonium ion.

In other embodiments, the at least one salt of the present invention may be chosen from silicates. Suitable silicates include, but are not limited to, metal silicates, organic silicates and polyatomic silicates.

Within the meaning of the present disclosure, "salt" is understood to include, but not limited to, the oxides and hydroxides of metals and the salts proper that can result from the action of an acid on a metal. In some embodiments, the at least one salt is not an oxide. In some embodiments, the at least one salt is not a hydroxide. Mention may be made, among the salts, of halides, such as chlorides, fluorides and iodides, sulfates, phosphates, lactates, acetates, glycinates, aspartates, nitrates, perchlorates, carbonates, hydrogen carbonates, silicates, borates and salts of carboxylic acids and polymeric complexes which can support said salts, and also their mixtures.

The salts of carboxylic acids which can be used in the disclosure also include salts of hydroxylated carboxylic acids, such as gluconate.

Mention may be made, as example of polymeric complexes which can support said salts, of manganese pyrrolidonecarboxylate.

One particularly preferred salt of the present invention is sodium sulfate.

The at least one salt of the present invention can be present in an amount ranging from about 0.1% to about 40% by weight or such as from about 0.5% to about 30% by weight, or, such as from about 1% to about 20% by weight, or such as from about 1% to about 10% by weight, based on the total weight of the composition.

It was surprisingly found that when the at least one salt is employed in the compositions of the present invention, less amounts of the alkaline agent and/or the oxidizing agent are necessary in order to achieve the desired degree of lift or lightening of the color of keratinous substrates. This would be more desirable since higher levels of the alkaline agent and/or oxidizing agent could result in more damage to the hair.

Moreover, when both the at least one salt and an oxidizing agent are present in the compositions of the present invention, peroxy compounds such as peroxyacids and peroxysalts, for example, peroxyborates, peroxycarbonates and peroxysulfates, may form in said compositions.

Cationic Polymers

The composition according to the present invention can also comprise at least one cationic polymer.

In at least one embodiment, the at least one cationic polymer included in the composition of the disclosure is not chosen from cationic associative polymers. In other words, these cationic polymers do not comprise in their structure a pendent or terminal hydrophobic chain, for example of alkyl or alkenyl type, containing from 10 to 30 carbon atoms.

The at least one cationic polymer of the composition according to the disclosure can be chosen from, for example:

(1) homopolymers and copolymers derived from acrylic or methacrylic esters or amides and comprising at least one unit chosen from units of formulae (XVI), (XVII), (XVIII) and (IX):

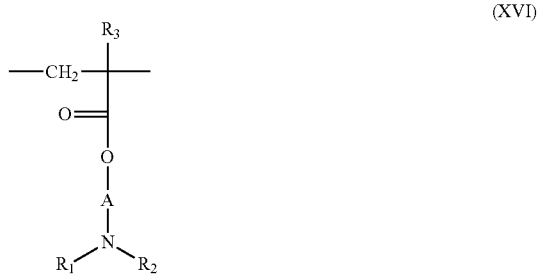

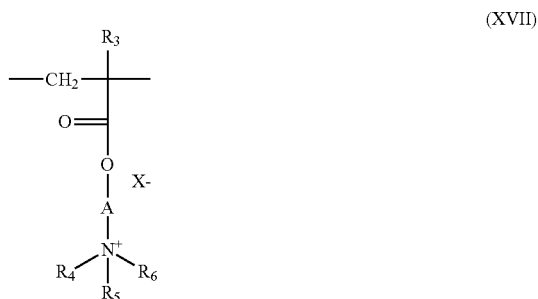

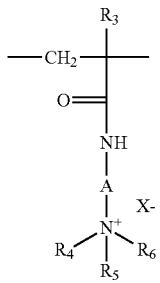 (XVIII)

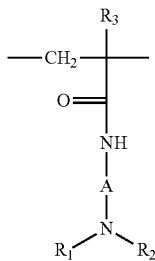 (XIX)

wherein:

$R_3$, which may be identical or different, denotes a hydrogen atom or a $CH_3$ radical;

A, which may be identical or different, represents a linear or branched $C_1$-$C_6$ and, for example, $C_2$-$C_3$ alkyl group or a $C_1$-$C_4$ hydroxyalkyl group;

$R_4$, $R_5$ and $R_6$, which may be identical or different, represent a $C_1$-$C_{18}$ alkyl group or a benzyl radical, such as a $C_1$-$C_6$ alkyl group;

$R_1$ and $R_2$, which may be identical or different, represent hydrogen or a $C_1$-$C_6$ alkyl group, for example methyl or ethyl;

$X^-$ denotes an anion derived from a mineral or organic acid, such as a methosulfate anion or a halide such as chloride or bromide.

The polymers of this family can also contain at least one unit derived from at least one comonomer which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among the polymers of this family, exemplary mention may be made of:

copolymers of acrylamide and of dimethylaminoethyl methacrylate quaternized with dimethyl sulfate or with a dimethyl halide, such as the product sold under the name HERCOFLOC by the company Hercules, the copolymers of acrylamide and of methacryloyloxyethyltrimethylammonium chloride described, for example, in EP 80 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or methacrylate copolymers, such as the products sold under the name GAFQUAT by the company ISP, for instance GAFQUAT 734 or GAFQUAT 755, or alternatively the products known as COPOLYMER 845, 958 and 937, dimethylaminoethyl methacrylate/vinylcaprolactam/vinylpyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, quaternized vinylpyrrolidone/dimethylaminopropylmethacrylamide copolymers such as the product sold under the name GAFQUAT HS 100 by the company ISP, and crosslinked polymers of methacryloyloxy($C_1$-$C_4$)alkyltri($C_1$-$C_4$)alkylammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, such as methylenebisacrylamide. In at least one embodiment, a crosslinked acrylamide/methacryloyloxyethyltrimethylammonium chloride copolymer (20/80 by weight) in the form of a dispersion containing 50% by weight of the copolymer in mineral oil can be used. This dispersion is sold under the name SALCARE® SC 92 by the company Ciba. In some embodiments, a crosslinked methacryloyloxyethyltrimethylammonium chloride homopolymer containing about 50% by weight of the homopolymer in mineral oil or in a liquid ester can be used. These dispersions are sold under the names SALCARE® SC 95 and SALCARE® SC 96 by the company Ciba.

Other examples are cellulose ether derivatives comprising quaternary ammonium groups, such as the polymers sold under the names JR (JR 400, JR 125, JR 30M) or LR (LR 400, LR 30M) by the company Union Carbide Corporation.

(2) copolymers of cellulose or cellulose derivatives grafted with a water-soluble quaternary ammonium monomer, such as hydroxymethyl-, hydroxyethyl- or hydroxy-propylcelluloses grafted, for instance, with a methacryloylethyltrimethylammonium, methacrylamidopropyltrimethylammonium or dimethyldiallylammonium salt. These are sold under the name CELQUAT L 200 and CELQUAT H 100 by the company National Starch.

(3), non-cellulose cationic polysaccharides, such as guar gums containing trialkylammonium cationic groups. Such products are sold, for example, under the trade names JAGUAR C13S, JAGUAR C15, JAGUAR C17 and JAGUAR C162 by the company Meyhall.

(4) polymers of piperazinyl units and of divalent alkylene or hydroxyalkylene radicals.

(5) water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 to 0.35 mol per amine group of the polyamino amide; these polyamino amides can be alkylated or, if they contain at least one tertiary amine function, they can be quaternized. Exemplary mention may be made of the adipic acid/dimethylaminohydroxypropyl/diethylenetriamine polymers sold under the name CARTARETINE F, F4 or F8 by the company Sandoz.

(6) the polymers obtained by reaction of at least one polyalkylene polyamine containing two primary amine groups and at least one secondary amine group with a dicarboxylic acid chosen from diglycolic acid and saturated $C_3$-$C_8$ aliphatic dicarboxylic acids. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Polymers of this type are sold, for example, under the name HERCOSETT 57, PD 170 or DELSETTE 101 by the company Hercules.

(7) cyclopolymers of alkyldiallylamine and of dialkyldiallylammonium, such as the homopolymers or copolymers containing, as main constituent of the chain, at least one unit corresponding to formula (XX) or (XXI):

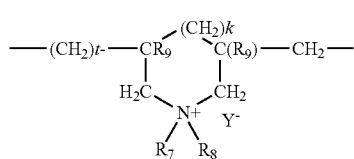

(XX)

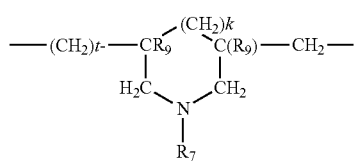

(XXI)

wherein formulae k and t are equal to 0 or 1, the sum k+t being equal to 1; $R_9$ denotes a hydrogen atom or a methyl radical; $R_7$ and $R_8$, independently of each other, denote a $C_1$-$C_8$ alkyl group, a hydroxyalkyl group in which the alkyl group is $C_1$-$C_5$, an amidoalkyl group in which the alkyl is $C_1$-$C_4$; or $R_7$ and $R_8$ denote, together with the nitrogen atom to which they are attached, a heterocyclic group such as piperidyl or morpholinyl; in at least one embodiment $R_7$ and $R_8$, independently of each other, denote a $C_1$-$C_4$ alkyl group; $Y^-$ is an organic or mineral anion such as bromide, chloride, acetate, borate, citrate, tartrate, bisulfate, bisulfite, sulfate or phosphate.

Among the polymers defined above, exemplary mention may be made of the dimethyldiallylammonium chloride homopolymer sold under the name MERQUAT® 100 and MERQUAT® 280 by the company Nalco (and its homologues of low weight-average molecular mass) and the copolymers of diallyldimethylammonium chloride and of acrylamide, sold under the name MERQUAT® 550.

(8) quaternary diammonium polymers containing repeating units of formula (XXII):

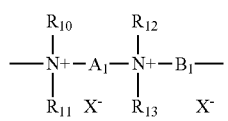

(XXII)

wherein:

$R_{10}$, $R_{11}$, $R_{12}$ and $R_{13}$, which may be identical or different, represent $C_1$-$C_6$ aliphatic, alicyclic or arylaliphatic radicals or hydroxyalkylaliphatic radicals wherein the alkyl radical is $C_1$-$C_4$, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D wherein $R_{14}$ is an alkylene and D is a quaternary ammonium group;

$A_1$ and $B_1$ represent $C_2$-$C_6$ polymethylene groups which are linear or branched, saturated or unsaturated, and which optionally contain, linked to or intercalated in the main chain, at least one aromatic ring or at least one atom chosen from oxygen and sulfur atom or at least one group chosen from sulfoxide, sulfone, disulfide, amino, alkylamino, hydroxyl, quaternary ammonium, ureido, amide and ester groups, and $X^-$ denotes an anion derived from a mineral or organic acid;

$A_1$, $R^{10}$ and $R_{12}$ can form, with the two nitrogen atoms to which they are attached, a piperazine ring;

and wherein, if $A_1$ denotes a linear or branched, saturated or unsaturated alkylene or hydroxyalkylene radical, $B_1$ can also denote a group —$(CH_2)_n$—CO-D-OC—$(CH_2)_n$— wherein n is a number ranging from 1 to 6, and D is chosen from:

a) a glycol residue of formula: —O—Z—O—, where Z denotes a linear or branched hydrocarbon-based radical or a group corresponding to one of the following formulae: —$(CH_2$—$CH_2$—O$)_x$—$CH_2$—$CH_2$—; or —[$CH_2$—CH($CH_3$)—O$]_y$—$CH_2$—CH($CH_3$)—, where x and y denote an integer ranging from 1 to 4, representing a defined and unique degree of polymerization or any number ranging from 1 to 4 representing an average degree of polymerization;

b) a bis-secondary diamine residue such as a piperazine derivative;

c) a bis-primary diamine residue of formula: —NH—Y—NH—, wherein Y denotes a linear or branched hydrocarbon-based radical, or alternatively the radical —$CH_2$—$CH_2$—S—S—$CH_2$—$CH_2$—; and d) a ureylene group of formula: —NH—CO—NH—.

In at least one embodiment, $X^-$ is an anion such as chloride or bromide.

These polymers, for example, have a number-average molecular mass ranging from 1000 to 100,000.

In some embodiments, polymers are used that consist of repeating units corresponding to formula (XXIII):

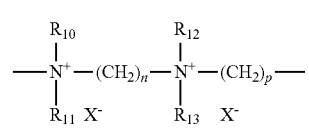

(XXIII)

wherein $R_{10}$, $R_{11}$, $R_{12}$ and $R_{13}$, which may be identical or different, denote a $C_1$-$C_4$ alkyl or hydroxyalkyl radical, n and p are integers ranging from 2 to 6, and $X^-$ is an anion derived from a mineral or organic acid.

In at least one embodiment, the at least one cationic polymer corresponding to this family comprise repeating units of formulae (W) and (U):

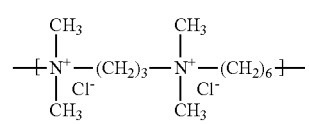

(W)

for example those whose molecular weight, determined by gel permeation chromatography, ranges from 9,500 to 9,900;

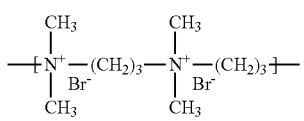

(U)

for instance those whose molecular weight, determined by gel permeation chromatography, is 1200.

(9) polyquaternary ammonium polymers consisting of repeating units of formula (XIV):

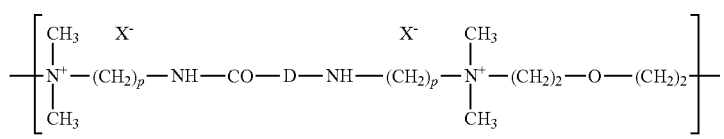

wherein p denotes an integer ranging from 1 to 6, D may be zero or may represent a group —(CH$_2$)$_r$—CO— wherein r denotes a number ranging from 1 to 6, and X$^-$ is an anion.

Such polymers may be prepared according to the processes described in U.S. Pat. Nos. 4,157,388, 4,702,906 and 4,719,282. They are described, for example, in patent application EP 122 324.

Among these polymers, examples that may be mentioned include the products MIRAPOL A 15, MIRAPOL AD1, MIRAPOL AZ1 and MIRAPOL 175 sold by the company Miranol.

(10) quaternary polymers of vinylpyrrolidone and of vinylimidazole, for instance the products sold under the names LUVIQUAT FC 905, FC 550 and FC 370 by the company BASF.

(11) vinylamide homopolymers or copolymers, such as partially hydrolysed vinylamide homopolymers such as poly(vinylamine/vinylamide)s.

(12) cationic polyurethane derivatives, for example those of elastic nature formed from the reaction:

(a1) of at least one cationic unit resulting from at least one tertiary or quaternary amine bearing at least two reactive functions containing labile hydrogen, (a2) of at least one mixture of at least two different nonionic units bearing at least two reactive functions containing labile hydrogen, for instance chosen from hydroxyl groups, primary or secondary amine groups, and thiol groups, and (b) of at least one compound comprising at least two isocyanate functions.

(13) Other cationic polymers that may be used in the context of the disclosure include, for example, cationic proteins or cationic protein hydrolysates, polyalkyleneimines, such as polyethyleneimines, polymers containing vinylpyridine or vinylpyridinium units, and chitin derivatives.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR CO 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5 to about 10% by weight, and more preferably from about 1 to about 5% by weight, based on the total weight of the composition.

The ready-to-use composition can also comprise other compounds constituting the cosmetically acceptable medium. This cosmetically acceptable medium comprises water or a mixture of water and at least one cosmetically acceptable organic solvent.

As examples of organic solvents, non-limiting mentions can be made of alcohols such as ethyl alcohol, isopropyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

The ready-to-use composition according to the disclosure can also comprise at least one additive used conventionally in compositions for application onto hair.

"Additive" means a substance that is added, different from the compounds already mentioned.

As examples of additives that can be used, non-limiting mentions can be made of surfactants, antioxidants or reducing agents, penetrating agents, sequestering agents, perfumes, buffers, dispersants, conditioners, such as for example volatile or non-volatile, modified or unmodified silicones, film-forming agents, ceramides, preservatives, opacifiers, and antistatic agents.

The ready-to-use composition according to the disclosure can be in various forms, such as in the form of liquids, creams, gels, lotions or paste.

The method of the present disclosure is a method comprising applying the ready-to-use composition according to the present disclosure onto the keratinous substrates. The oxidizing agent can be added at the moment of use or it can be used simultaneously or sequentially with the other compounds of the ready-to-use composition of the disclosure.

After a resting time on the keratinous substrates, for example, ranging from about 1 to 60 minutes, such as from about 5 to 45 minutes, the keratinous substrates are rinsed, optionally washed with shampoo and rinsed again, then dried.

The ready-to-use compositions according to the disclosure can result from mixing at least two compositions, including an oxidizing composition comprising at least one oxidizing agent as defined previously or including a composition comprising, in a cosmetically acceptable medium, at least one salt as defined previously. The ready-to-use compositions can be obtained before application onto the keratinous substrates, or simultaneously with application to the keratinous substrates.

Typically, the oxidizing agent of the present invention is provided in the form of an oxidizing composition.

In one particular embodiment, the oxidizing composition is aqueous or is in the form of an emulsion.

In another embodiment, the oxidizing composition is substantially anhydrous.

The term "substantially anhydrous" means that the oxidizing composition is either completely free of water or contains no appreciable amount of water, for example, no more than 5% by weight, or no more than 2% by weight, or no more than, 1% by weight, based on the weight of the oxidizing composition. It should be noted that this refers for example to bound water, such as the water of crystallization of the salts or traces of water absorbed by the raw materials used in the preparation of the compositions according to the disclosure.

The oxidizing composition can contain at least one solvent, chosen from water, organic solvents, and mixtures thereof.

When the oxidizing composition is substantially anhydrous, the oxidizing composition may comprise at least one solvent chosen from organic solvents.

Suitable organic solvents for use in the oxidizing composition include ethanol, isopropyl alcohol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The at least one solvent may, for example, be present in an amount ranging from 0.5% to 70% by weight, such as from 2% to 60% by weight, preferably from 5 to 50% by weight, relative to the total weight of the oxidizing composition.

The oxidizing composition may be in the form of a powder, gel, liquid, foam, lotion, cream, mousse, and emulsion.

The pH of the oxidizing composition can range from 2 to 12, such as from 6 to 11, and it may be adjusted to the desired value using acidifying/alkalizing agents that are well known in the art.

In some embodiments, the method of the present disclosure involves providing a pre-treatment composition containing, in a cosmetically acceptable medium, at least one salt of the present invention, and applying the pre-treatment composition onto keratinous substrates prior to the application of the ready-to-use composition of the present invention.

The present invention also provides a kit, comprising:

a first unit containing in a cosmetically acceptable medium: at least one phospholipid; at least one nonionic surfactant; at least one anionic silicone; optionally, at least one thickening agent; optionally, at least one alkaline agent; optionally, at least one fatty substance other than a fatty acid; and optionally, at least one salt; and a second unit comprising at least one oxidizing agent and optionally, at least one fatty substance other than a fatty acid.

In some embodiments, the second unit comprising the oxidizing agent can comprise a substantially anhydrous composition. The term "substantially anhydrous" means that the oxidizing composition is either completely free of water or contains no appreciable amount of water, for example, no more than 5% by weight, or no more than 2% by weight, or no more than 1% by weight, based on the weight of said composition. It should be noted that this refers for example to bound water, such as the water of crystallization of the salts or traces of water absorbed by the raw materials used in the preparation of the compositions according to the disclosure.

The kit of the present invention can further comprise a third unit containing, in a cosmetically acceptable medium, at least one salt of the present invention.

The kit of the present invention can be equipped with at least one of applicators for delivery of the desired mixture onto the hair, such as the applicators described in French Patent No. 2 586 913.

The invention will be further clarified by the following examples, which are intended to be illustrative of the invention, but' not limiting thereof.

EXAMPLES

The following example is intended for illustrative purposes only, and is not meant to unduly limit the scope of the invention in any way.

Example 1

Color Lift Study

Ten (10) g of each of the compositions below were mixed in a 1:1 ratio with a 20 volume hydrogen peroxide developer. The pH of each final mixture was about 10. Each final mixture was then applied onto a designated swatch of natural brown level 3 hair 0.5 cm width, 15 cm length), commercially available from IHIP, International Hair Importers.

| Ingredient | Formula A | Formula B | Formula C |
|---|---|---|---|
| Lecithin | 1.0% | 1.0% | 1.0% |
| PPG-5 Ceteth-20 | 11% | 11% | 11% |
| Dimethicone PEG-7 Phosphate | 5.0% | 5.0% | 5.0% |
| Mineral oil | 1.0% | 1.0% | 1.0% |
| Ethanolamine | 3.0% | 3.0% | 4.0% |
| Sodium Sulfate | 1.0% | — | — |
| Water | Q.S. | Q.S. | Q.S. |

Two control formulas comprising the base formula of a commercial product, L'Oréal Preference™ were also applied onto separate hair swatches. Control formula 1 contained 4% ethanolamine as the alkaline agent and control formula 2 contained 10.2% ammonium hydroxide as the alkaline agent.

All swatches were processed for 30 minutes at a 27° C. heating plate, rinsed for 1 minute (80 gph, 32° C.), and dried. Color measurements were taken before and after treatment as L values which correspond to the degree of lightness of the color of the hair, using Konica Minolta Spectrophotometer.

The final ΔL (change in L) value measurements on the swatches treated with Formulas A to C were 7.98, 4.23, and 7.38, respectively. The final ΔL (change in L) value measurements on the swatches treated with control formulas 1 and 2 were 4.21 and 9.63, respectively. A greater ΔL value indicates a greater change in the lightness of the color of the hair which indicates a greater lift in color. The results show that formulas A and C lightened the color of the hair significantly better than the control formula 1. As for formula B, this had a lightening effect that was comparable to that of control formula 1; however, it required less amount of the alkaline agent, ethanolamine, to achieve the same degree of lightening which is more advantageous since lower levels of the alkaline agent are more desirable.

Moreover, formula A, which contained sodium sulfate, lightened the color of the hair significantly better than formula B which had the same amount of the alkaline agent and had a comparable lightening effect to that of C which had a higher amount of the alkaline agent but did not contain sodium sulfate. As for control formula 2, this formula contained a higher level of alkaline agent, that is, 10.2% of ammonium hydroxide, which is less desirable.

It will be apparent to those skilled in the art that numerous modifications and variations can be made without departing from the spirit or scope of the invention.

What is claimed is:

1. A ready-to-use aqueous composition for lifting color of and/or imparting shine onto keratinous substrates, the composition consisting essentially of, in a cosmetically acceptable medium:
   (a) from about 0.5 to about 10% by weight of at least one phospholipid chosen from lecithin, cocamidopropyl PG-dimonium chloride phosphate, sodium coco PG-dimonium chloride phosphate, stearamidopropyl PG-dimonium chloride phosphate, sodium borageamidopropyl PG-dimonium chloride phosphate and linoleamidopropyl PG-dimonium chloride phosphate;
   (b) from about 1 to about 20% by weight of at least one nonionic surfactant having an HLB of at least about 8;
   (c) from about 0.5 to about 40% by weight of at least one anionic silicone chosen from a silicone phosphate, a silicone carboxylate, a silicone sulfate, a silicone sulfosuccinate and a silicone sulfonate;
   (d) from about 0.1 to about 20% by weight of at least one oxidizing agent;
   (e) from about 0.1 to about 10% by weight of at least one thickening agent;
   (f) from about 1 to about 10% by weight of at least one alkaline agent chosen from organic amines, organic amine salts, ammonium salts, alkali metal phosphates, alkali metal carbonates and alkali metal carboxylates;
   (g) at least one fatty substance other than a fatty acid; and
   (h) from about 0.5 to about 30% by weight of at least one salt chosen from halides, sulfates, phosphates, lactates, acetates, glycinates, aspartates, nitrates, perchlorates, carbonates, hydrogen carbonates, silicates, borates, and carboxylates;
   all weights being based on the weight of the composition.

2. The composition of claim 1, wherein (a) is lecithin.

3. The composition of claim 1, wherein phospholipid is linoleamidopropyl PG-dimonium chloride phosphate.

4. The composition of claim 1, wherein (b) is chosen from alkoxylated fatty alcohols.

5. The composition of claim 1, wherein (b) is chosen from PPG-5 ceteth-20, laureth-3, laureth-23, ceteth-10, steareth-10, and steareth-2, steareth-100, beheneth-5 and beheneth-10.

6. The composition of claim 1, wherein (c) is a silicone phosphate chosen from dimethicone PEG-7 phosphate and dimethicone PEG-8 phosphate.

7. The composition of claim 1, chosen from peroxides, bromates of alkali metals, ferricyanides of alkali metals, peroxygenated salts, oxidoreduction enzymes, and oxygen in air.

8. The composition of claim 1, wherein (d) is hydrogen peroxide.

9. The composition of claim 1, wherein (e) is chosen from a polymeric thickener and a non-polymeric thickener.

10. The composition of claim 1, wherein (f) is chosen from organic amines.

11. The composition of claim 10, wherein (f) is an organic amines chosen from monoethanolamine, diethanolamine, triethanolamine, N-d imethylaminoethanolamine, 2-amino-2-methyl-1-propanol, 2-amino-2-methyl-1,3-propanediol, 1,3-diaminopropane, 1,3-diamino-2-propanol, arginine, lysine, histidine, pyridine, piperidine, imidazole, 1,2,4-triazole, tetrazole, benzimidazole, 1,1-dimethyl guanidine, and 1,1,-diethylguanidine.

12. The composition of claim 1, wherein (g) is chosen from alkanes, hydrocarbon oils, silicones, fatty alcohols, esters of fatty acids, esters of fatty alcohol, vegetable oils and non-silicone waxes.

13. The composition of claim 1, wherein (g) is mineral oil.

14. The composition of claim 1, wherein (h) is sodium sulfate.

15. The composition of claim 1, wherein the pH of the composition is from about 2 to about 12.

16. The composition of claim 1, wherein the pH of the composition is less than 7.

17. The composition of claim 1, wherein the pH of the composition is at least 7.

18. The composition of claim 1, wherein the composition is substantially free of ammonia.

* * * * *

UNITED STATES PATENT AND TRADEMARK OFFICE
CERTIFICATE OF CORRECTION

| | | |
|---|---|---|
| PATENT NO. | : 8,802,070 B2 | Page 1 of 2 |
| APPLICATION NO. | : 13/167954 | |
| DATED | : August 12, 2014 | |
| INVENTOR(S) | : Siliu Tan, Nghi Van Nguyen and Sawa Hashimoto | |

It is certified that error appears in the above-identified patent and that said Letters Patent is hereby corrected as shown below:

In the Claims

Col. 29, line 22, Claim 1: "A ready-to-use aqueous composition for lifting color of and/or imparting shine onto keratinous substrates, the composition consisting essentially of," should read --A method of lifting color of keratinous substrates, comprising applying onto the keratinous substrates a ready-to-use aqueous composition, containing,--

Col. 30, line 5, Claim 2: "The composition of" should read --The method of--

Col. 30, line 6, Claim 3: "The composition of" should read --The method of--

Col. 30, line 8, Claim 4: "The composition of" should read --The method of--

Col. 30, line 10, Claim 5: "The composition of" should read --The method of--

Col. 30, line 14, Claim 6: "The composition of" should read --The method of--

Col. 30, line 17, Claim 7: "The composition of claim 1, chosen from peroxides," should read --The method of claim 1, wherein (d) is chosen from peroxides,--

Col. 30, line 20, Claim 8: "The composition of" should read --The method of--

Col. 30, line 22, Claim 9: "The composition of" should read --The method of--

Col. 30, line 24, Claim 10: "The composition of" should read --The method of--

Col. 30, line 26, Claim 11: "The composition of claim 10, wherein (f) is an organic amines chosen" should read as --The method of claim 10, wherein the organic amines are chosen--

Signed and Sealed this
Sixteenth Day of December, 2014

Michelle K. Lee
*Deputy Director of the United States Patent and Trademark Office*

CERTIFICATE OF CORRECTION (continued)
U.S. Pat. No. 8,802,070 B2

Col. 30, line 28, Claim 11: "N-d imethylaminoethanolamine" should read --N-dimethylaminoethanolamine--

Col. 30, line 34, Claim 12: "The composition of" should read --The method of--

Col. 30, line 38, Claim 13: "The composition of" should read --The method of--

Col. 30, line 39, Claim 14: "The composition of" should read --The method of--

Col. 30, line 41, Claim 15: "The composition of" should read --The method of--

Col. 30, line 43, Claim 16: "The composition of" should read --The method of--

Col. 30, line 45, Claim 17: "The composition of" should read --The method of--

Col. 30, line 47, Claim 18: "The composition of" should read --The method of--